United States Patent
Hill et al.

(10) Patent No.: US 12,211,618 B2
(45) Date of Patent: Jan. 28, 2025

(54) METHODS AND SYSTEMS FOR TREATING CANCER BASED ON RESPONSE PREDICTION USING LIGHT SCATTERING TECHNOLOGY

(71) Applicants: THE UNIVERSITY OF ROCHESTER, Rochester, NY (US); HARMONIGENIC CORPORATION, Rochester, NY (US)

(72) Inventors: Robert Lawrence Hill, Rochester, NY (US); Edward Bernard Brown, Rochester, NY (US); David Hicks, Rochester, NY (US); Brandon Buscaglia, Rochester, NY (US); Bradley Turner, Rochester, NY (US); Danielle Desa, Rochester, NY (US)

(73) Assignees: THE UNIVERSITY OF ROCHESTER, Rochester, NY (US); HARMONIGENIC CORPORATION, Rochester, NY (US)

( * ) Notice: Subject to any disclaimer, the term of this patent is extended or adjusted under 35 U.S.C. 154(b) by 934 days.

(21) Appl. No.: 17/292,109

(22) PCT Filed: Nov. 8, 2019

(86) PCT No.: PCT/US2019/060422
§ 371 (c)(1),
(2) Date: May 7, 2021

(87) PCT Pub. No.: WO2020/097433
PCT Pub. Date: May 14, 2020

(65) Prior Publication Data
US 2021/0398673 A1    Dec. 23, 2021

Related U.S. Application Data

(60) Provisional application No. 62/795,828, filed on Jan. 23, 2019, provisional application No. 62/758,408, filed on Nov. 9, 2018.

(51) Int. Cl.
| | |
|---|---|
| *G16H 10/00* | (2018.01) |
| *A61B 5/00* | (2006.01) |
| *G01N 21/63* | (2006.01) |
| *G01N 33/483* | (2006.01) |
| *G16H 10/40* | (2018.01) |
| *G16H 20/40* | (2018.01) |
| *G16H 30/40* | (2018.01) |
| *G16H 50/20* | (2018.01) |
| *G16H 50/30* | (2018.01) |

(52) U.S. Cl.
CPC .......... *G16H 50/20* (2018.01); *A61B 5/4842* (2013.01); *G01N 21/636* (2013.01); *G01N 33/4833* (2013.01); *G16H 10/40* (2018.01); *G16H 20/40* (2018.01); *G16H 30/40* (2018.01); *G16H 50/30* (2018.01)

(58) Field of Classification Search
None
See application file for complete search history.

(56) References Cited

U.S. PATENT DOCUMENTS

2008/0015448 A1* 1/2008 Keely .................. A61B 5/0068
                                                             600/562
2017/0020462 A1* 1/2017 Brown, III ............. A61B 1/044

OTHER PUBLICATIONS

Wu et al., Quantitative evaluation of redox ratio and collagen characteristics during breast cancer chemotherapy using two-photon intrinsic imaging, Biomedical Optics Express, vol. 9, No. 3, Mar. 1, 2018, pp. 1-14 (Year: 2018).*
Campagnola, Paul; Second Harmonic Generation Imaging Microscopy: Applications to Diseases Diagnostics, Analytical Chemistry, 2011, 83, pp. 3224-3231. (Year: 2011).*
Li et al., Monitoring neoadjuvant therapy responses in rectal cancer using multimodal nonlinear optical microscopy, Oncotarget, 2017, vol. 8, No. 63, pp. 107323-107333. (Year: 2017).*
Communication under Rule 71(3) received in related EP Application No. 19836 084.4 dated May 9, 2023.
International Search Report and Written Opinion issued in PCT/US2019/060422, dated Apr. 20, 2020, 17 pages.
Lian-Huang Li et al: "Monitoring neoadjuvant therapy responses in rectal cancer using multimodal nonlinear optical microscopy", Oncotarget, vol. 8, No. 63, Dec. 5, 2017, pp. 107323-107333.
Lian-Huang Li: "Multiphoton microscopy for tumor regression grading after neoadjuvant treatment for colorectal carcinoma", World Journal of Gastroenterology, vol. 21, No. 14, Jan. 1, 2015, p. 4210.
Jason Z. Cui et al: "Quantification of aortic and cutaneous elastin and collagen morphology in Marfan syndrome by multiphoton microscopy", Journal of Structural Biology, vol. 187, No. 3, Sep. 1, 2014, pp. 242-253.
Pantazis P, Maloney J, Wu D, Fraser SE. Second harmonic generating (SHG) nanoprobes for in vivo imaging. Proceedings of the National Academy of Sciences of the United States of America. 2010; 107(33):14535-14540. doi:10.1073/pnas.1004748107.
Han X, Burke RM, Zettel ML, Tang P, Brown EB. Second harmonic properties of tumor collagen: determining the structural relationship between reactive stroma and healthy stroma. Opt Express. 2008;16(3):1846-59. PubMed PMID: 18542263.
Williams RM, Zipfel WR, Webb WW. Interpreting second-harmonic generation images of collagen I fibrils. Biophys J. 2005;88(2):1377-86. doi: 10.1529/biophysj.104.047308. PubMed PMID: 15533922; PMCID: PMC1305140.

(Continued)

*Primary Examiner* — Gary Counts
(74) *Attorney, Agent, or Firm* — Meunier Carlin & Curfman LLC

(57) ABSTRACT

Disclosed are methods and systems that make use of light scattering techniques, such as the use of a multiphoton laser-scanning microscope, to quantify the scattering directionality of second harmonic generation (SHG) from biopsy samples of cancer in order to predict efficacy of neoadjuvant chemotherapy.

16 Claims, 7 Drawing Sheets

(56) References Cited

OTHER PUBLICATIONS

Burke K, Smid M, Dawes RP, et al. Using second harmonic generation to predict patient outcome in solid tumors. BMC Cancer. 2015;15:929. doi:10.1186/s12885-015-1911-8.
Sage, D. OrientationJ: A series of ImageJ plugins for directional image analysis. Biomedical Image Group at EPFL, Switzerland.

* cited by examiner

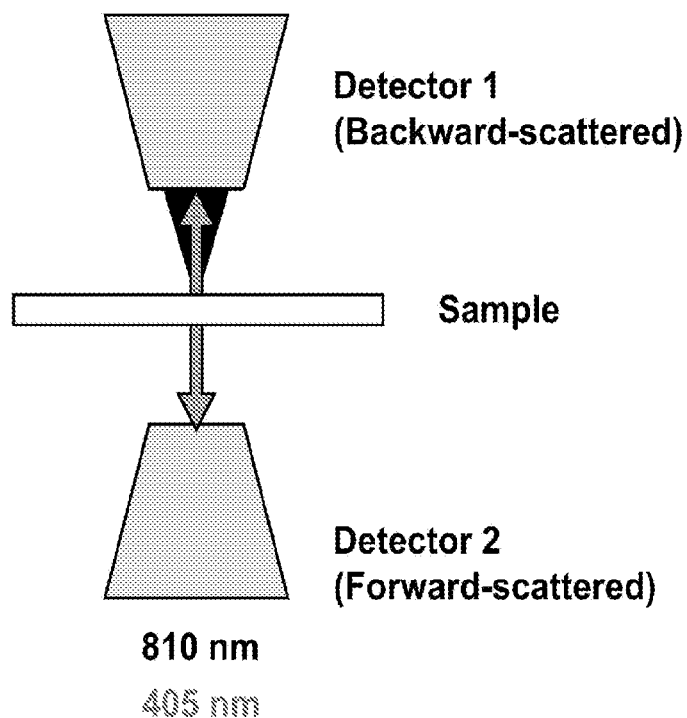
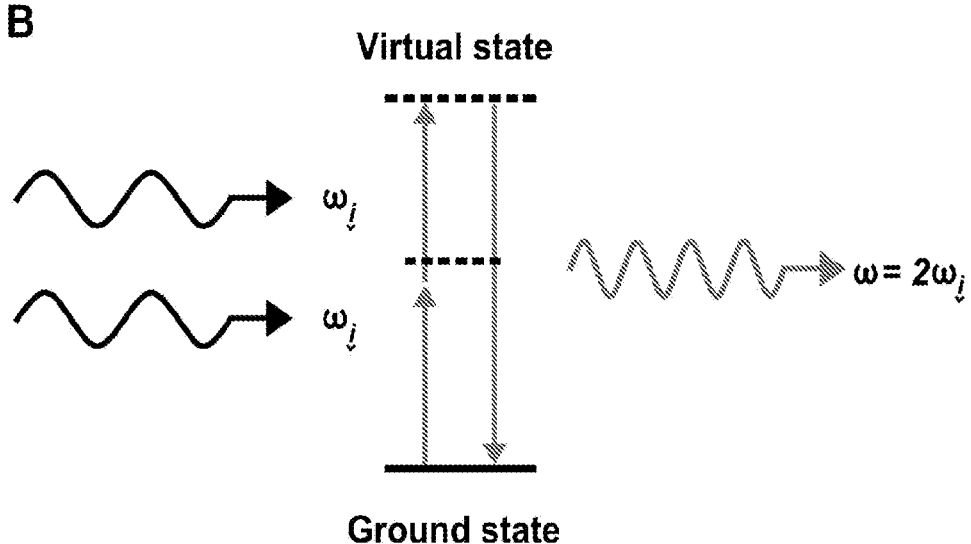
FIGS. 1A-B

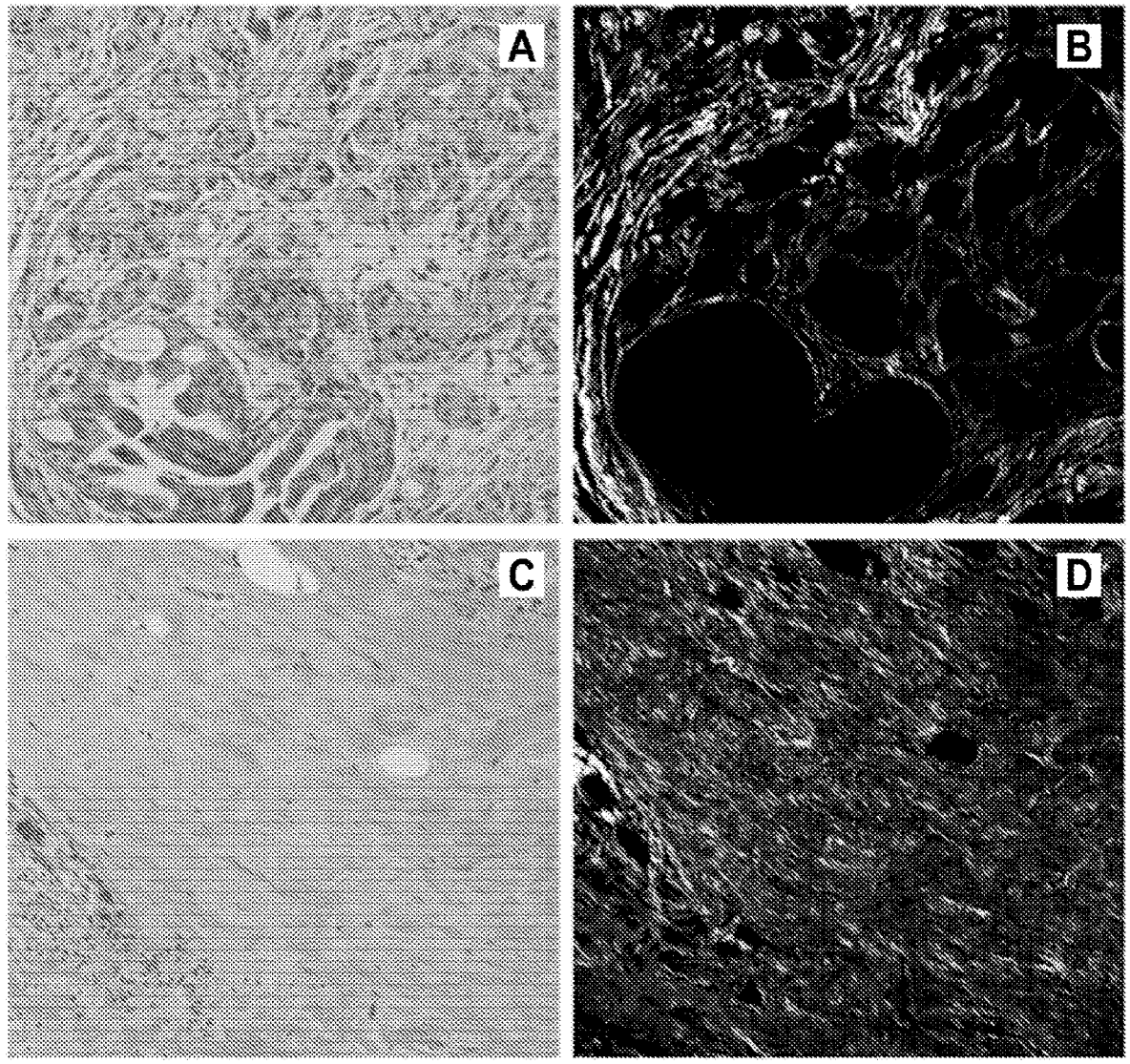
FIGS. 3A-D

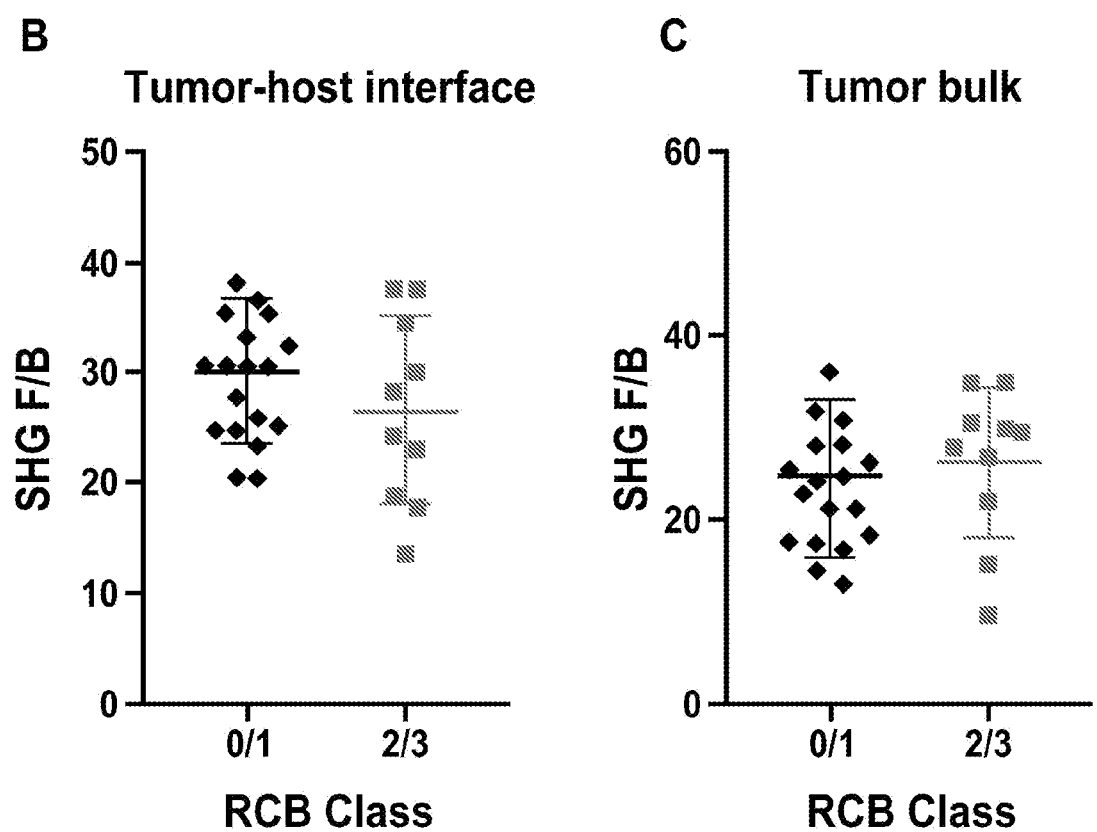
FIGS. 4B-C

METHODS AND SYSTEMS FOR TREATING CANCER BASED ON RESPONSE PREDICTION USING LIGHT SCATTERING TECHNOLOGY

CROSS-REFERENCE TO RELATED APPLICATIONS

This is a national stage application filed under 35 U.S.C. § 371 of PCT International Application No. PCT/US2019/060422, filed Nov. 8, 2019 and titled "METHODS AND SYSTEMS FOR TREATING CANCER BASED ON RESPONSE PREDICTION USING LIGHT SCATTERING TECHNOLOGY," which claims benefit of U.S. Provisional Application No. 62/758,408, filed Nov. 9, 2018, and U.S. Provisional Application No. 62/795,828, filed Jan. 23, 2019, which are hereby incorporated herein by reference in their entirety.

GOVERNMENT SUPPORT CLAUSE

This invention was made with government support under BCRP Grant No. W81XWH-17-1-0011, awarded by The Department of Defense. The government has certain rights in the invention.

BACKGROUND

In an aggressive cancer such as breast cancer, timely treatment greatly enhances the likelihood of a successful outcome, and multiple therapies are applied concurrently. In the case of breast cancer, the suspicious breast lesion is biopsied and determined to be malignant, and the cancer is typed. One treatment approach following biopsy is neoadjuvant therapy including administration of a biologic agent such as bevacizumab (indicated for HER2 negative patients) or trastuzumab (indicated for HER2 positive patients) is administered in combination with chemotherapy for several weeks, followed by surgical removal of the lesion. A pathological complete response (pCR), in which no malignant tumor tissue or metastasis is detected in the patient, is the desired outcome. In practice, whether pCR is achieved in a given patient is not determined until after the surgery and subsequent examination of the excised tumor.

If the neoadjuvant therapy is ultimately not effective, then valuable time has been lost by not doing the surgical resection first, and the likelihood of an ultimately successful outcome has diminished. In view of this, various assessments are typically performed during the therapy in order to assess likely effectiveness. The tumor may be monitored by a series of imaging sessions performed over the course of the therapy using magnetic resonance (MR) imaging or another suitable imaging technique. A functional imaging modality such as positron emission tomography (PET) or single photon emission computed tomography (SPECT) may be applied to assess functional aspects, e.g. angiogenesis. Additional biopsies may be performed over the course of the treatment regimen to periodically assess the tumor.

While these approaches are useful, they have some drawbacks. Medical imaging is expensive, involves various interpretive inferences, and can be stressful for the patient. Biopsies are invasive. As the chemotherapy regimen progresses, the potential for introducing infection during biopsy increases over time, as does the potential for adverse patient response to any such infection. These techniques also usually do not provide a meaningful assessment until a substantial way through the course of treatment, and the results can be unclear, especially during the early stages of treatment. For example, medical images may indicate that the tumor is not shrinking as expected; but the treatment may nonetheless ultimately achieve pCR. If evidence accumulating over time increasingly suggests that the treatment will not be effective, the patient's physician must make the difficult choice of continuing with a therapy regimen that may not work, or alternatively terminating or adjusting the therapy without knowing whether it would ultimately have been successful.

The use of genetic tests has been contemplated for correlating patient therapy response with expression of specific genes or microRNAs (miRNA) measured using gene arrays, immunohistochemistry, or reverse transcription-polymerase chain reaction (RT-PCR). Typically, these molecular markers are measured at baseline before the patient undergoes neoadjuvant therapy and these baseline measurements are used to stratify patients into groups that may or may not benefit from subsequent therapy. (Gene Expression Profiles in Paraffin-Embedded Core Biopsy Tissue Predict Response to Chemotherapy in Women With Locally Advanced Breast Cancer DOI: 10.1200/JCO.2005.02.0818 *Journal of Clinical Oncology* 23, no. 29 (October 2005) 7265-7277) However, these predictors from baseline breast core needle biopsies have not achieved sufficient specificity to be routinely used in the clinic. For the most common subtype of breast cancer that is known as invasive ductal carcinoma (IDC) estrogen receptor (ER) positive and HER2 negative, there is evidence that those predicted by Genomic Health Oncotype DX (RT-PCR 21 gene expression assay) recurrence score (RS) to respond to chemotherapy in the adjuvant setting are also more likely to achieve pCR (Chang J C, et al. Breast Cancer Res Treat. 2008; 108 (2):233-240) but due to the generally overall poor response to neoadjuvant chemotherapy for this most common subtype, IDC ER positive, HER2 negative breast cancer (also known as luminal A breast cancer), hormonal therapy alone is often used where shrinking the tumor before surgery is the goal. If a method could identify in this most common luminal A breast cancer, those that would respond to neoadjuvant chemotherapy by achieving pCR such a method would fill an unmet need in the market.

Using light scattering technology, a second-harmonic-generation-forward/backward (SHG F/B) ratio can be obtained from an object by performing only a single image scan. Two simultaneous SHG images (a forward propagating SHG "F" image and a back propagating SHG "B" image) are generated during the single image scan using separate detectors. The measurement of the ratio of the forward-propagating ("F") to backward propagating ("B") SHG signal (the "F/B ratio") has been used to study collagen fiber ordering in various tissue samples. The F/B ratio revealed the length scale of ordering in the fibers, and in the case of osteogenesis imperfecta, ovarian cancer, and breast cancer was able to be used to discriminate pathological tissue from healthy tissue. (LaComb et al. Quantitative Second Harmonic Generation Imaging of the Diseased State Osteogenesis Imperfecta: Experiment and Simulation. Biophysical Journal 2008 94(11) 4504-4514).

Dekker et al. (*Disorganised stroma determined on pretreatment breast cancer biopsies is associated with poor response to neoadjuvant chemotherapy: Results from the NEOZOTAC trial*, Molecular Oncology, 9, doi: 10.1016/j.molonc.2015.02.001) measure overall organization of collagen using conventional microscopy of H&E stained tumor stroma tissue, and it was concluded after measuring direction of the stromal collagen at many small areas that "Intratumoral stromal organisation determined using pretreatment breast cancer biopsies was related to pathological response to chemotherapy." While this method was predictive of treatment response for ER+ IDC breast cancer in the neoadjuvant setting, it relied on standard H&E or trichrome AZAN-staining for collagen fibers and does not use SHG. In fact SHG F/B ratios averaged point by point are independent of the direction of the collagen fibers inferred by looking at direction of cells observable in stained tissue slides and therefore F/B is not obviously related to stromal organization of collagen and based on measurements it is not.

However, what is needed in the art are methods for determining the best course for treating cancer, particularly HER2+ breast cancer, based on response prediction using SHG F/B ratios improving outcomes for those commonly treated with neoadjuvant chemotherapy. Luminal A breast cancer (ER+, HER2−), though not commonly treated with neoadjuvant chemotherapy due to an overall poor response of the population, could be treated individually with neoadjuvant chemotherapy if patients with treatable tumors could be selected, based on response prediction using SHG F/B ratios.

SUMMARY

In accordance with the purposes of the disclosed materials and methods, as embodied and broadly described herein, the disclosed subject matter, in one aspect, relates to a method of treating a subject with cancer, the method comprising: obtaining a sample from cancerous tissue of the subject; preparing the sample for a light scattering test; applying second harmonic generation (SHG) two photon scattering measurements from the sample to determine directionality of scattered photons; obtaining a signature score using selected data from SHG data; determining if the signature score falls above or below a reference level, wherein if the signature score is above the reference level, the subject is treated with neoadjuvant therapy, and if the signature score is below the reference level, the subject is subjected to surgical treatment.

Also disclosed is a system for evaluating a sample of tissue from a subject with cancer to determine treatment outcome using neoadjuvant chemotherapy, comprising: an SHG optical imaging device for generating correlated test image pairs in the forward and backward direction or test imaging data from the sample where each pixel represents the ratio of the forward to backward two photon light scatter intensities or photon counts from SHG; and a processor for analyzing said test image pairs or test imaging directional data from a point by point measurement of the sample, said processor using a quantitative algorithm for analyzing said test image or test imaging directional data for detection of a signature distribution of values from a region of interest (ROI) related to treatment outcome using neoadjuvant chemotherapy, wherein said signature distribution of values is used to generate a signature score.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 1A-C shows SHG signal. To generate SHG images, a red mode-locked laser, which has very short, intense pulses that allow for SHG is scanned over a region of interest (ROI) in a patient sample (A). Two red photons interact with fibrillar collagen in the tumor, producing one blue photon that scatters off the collagen in either the forward or backward direction (B). The SHG forward-to-backward (F/B) ratio is sensitive to fibril diameter, packing disorder, and spacing within collagen fibers (C). The blue photon is collected by one of two lenses and a forward-to-backward scattered ratio (F/B) is generated for each ROI.

FIG. 3A-D shows tumor bulk and tumor-host interface can be imaged with SHG microscopy. Core needle biopsies contain tissue located within the bulk of the tumor as well as within the tumor-host interface consisting mostly of collagen. Here, the same region of the tumor bulk is shown: A) transmitted light microscopy (H&E stain, 10×) and B) 2-photon SHG image of the same region (FOV=660 µm). In the same biopsy, a field of view containing the tumor-host interface is shown: C) transmitted light microscopy (H&E stain, 10×); and D) 2-photon SHG image of the same region in the collagenous tumor-host interface (FOV=660 µm).

FIG. 4A-B shows F/B taken from pre-treatment biopsies is associated with subsequent RCB class when measured in the tumor-host interface, but not when measured in the bulk of the tumor. SHG images taken in the tumor-host interface and tumor bulk were analyzed in two ways. The first method (A) utilizes a user-defined intensity threshold in both the forward and the backward correlated images to exclude pixels that are not within collagen fibers. The second method (B) uses the isotropy of an ROI to create a mask that includes collagen fibers. Using the intensity-based method, F/B was associated with RCB class in the tumor-host interface (Logistic regression, using RCB class 0/1 and 2/3 as binary variable, *p=0.035). In other words, the first method shows a difference between F/B from responders vs non-responders when measured in tumor-host interface but not in bulk, while the second method shows no difference in either.

FIG. 4C shows results from a second population of 35 luminal A (ER+, HER2−) IDC breast cancer patients where F/B taken from pre-treatment biopsies is also associated with subsequent RCB class when measured in the tumor-host interface, but not when measured in the bulk of the tumor. Analysis using the intensity-based method, F/B was associated with RCB class in the tumor-host interface (Logistic regression, using RCB class 0/1 and 2/3 as binary variable, *p=0.0404) but not in the bulk of the tumor (p=0.4393).

DETAILED DESCRIPTION

Figure 1C:
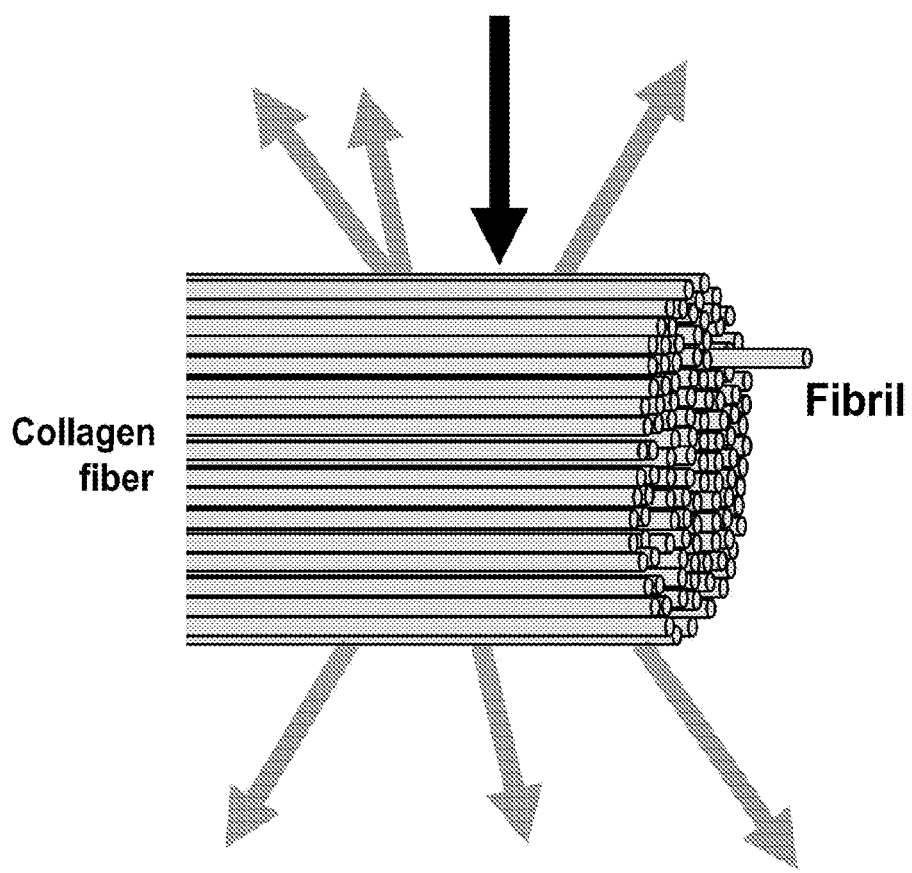

The methods and systems described herein may be understood more readily by reference to the following detailed description of specific aspects of the disclosed subject matter and the Examples and Figures included therein.

Before the present systems and methods are disclosed and described, it is to be understood that the aspects described below are not limited to specific products or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include, for example, domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, inhibit, or eliminate a particular characteristic or event (e.g., tumor growth or survival). The term "control" is used synonymously with the term "treat."

When used herein, the term "cancerous" is as generally understood in the art. For example, the term can refer to a clinical condition of an unregulated or misregulated cell or tumor wherein there is an abnormal ability to proliferate, differentiate, and or migrate. The term is intended to address a variety of stages of disease progression. Thus the term precancerous is envisioned as encompassed within the conceptual scope whether viewed as a distinct earlier stage with a different potential and/or different level of disease significance relative to cancerous or viewed as part of a connected pathway or continuum. In a particular example, a cancerous condition can include having a prepalpable breast mass, wherein the mass is a tumor or suspected tumor.

The term "anticancer" refers to the ability to treat or control cellular proliferation and/or tumor growth at any concentration.

The term "nonlinear" refers to photonic processes, such as fluorescence excitation or SHG scattering, that exhibit a rate that depends nonlinearly on the intensity of incident electromagnetic radiation. Nonlinear optical imaging methods useful in the present invention include, but are not limited to, multiphoton (MP) microscopy (two photon excitation, three photon excitation, etc.) and harmonic generation microscopy (second harmonic generation, third harmonic generation, fourth harmonic generation, etc.).

When used herein, the term "tissue sample" can refer to a portion of tissue from an animal subject. The sample can be intact and in situ, for example as part of a tissue or organ while remaining attached to the living animal. Alternatively, the sample can be an excised tissue portion which can optionally be further processed. In an embodiment, the excised sample is fixed. In an embodiment, the excised sample is stained, e.g., using conventional histopathology techniques. In an embodiment, the excised sample is frozen. In a particular embodiment, the sample is a mammalian breast tissue sample or epithelial tissue sample. In a preferred embodiment, the sample is a live or excised breast tissue portion which is structurally intact.

When used herein, the term "test tissue sample" generally refers to a tissue sample from a subject where a condition of the sample or the subject is unknown or suspected and it is desired to ascertain such condition. For example, a test tissue sample can be a breast sample from which a breast cancer diagnosis is to be determined.

When used herein, the term "reference tissue sample" generally refers to a tissue sample for which a condition has been ascertained. For example, the reference could correspond to a sample having a known positive condition or a known negative condition, or a stage of a disease or normal physiological process, thus serving as a control or point of comparison in the evaluation of a different sample.

When used herein, the term "reference level" indicates a level that has been assessed and serves as a point of comparison relative to a test level. For example, a reference level can be an amount or qualitative state as seen in a normal condition, a diseased condition, or as seen in a point along a continuum of conditions.

When used herein, the term "diagnosis" and other root word derivatives are as understood in the art and are further intended to include a general monitoring, characterizing and/or identifying a state of health or disease. The term is meant to encompass the concept of prognosis. For example, the diagnosis of breast cancer can include an initial determination and/or one or more subsequent assessments regardless of the outcome of a previous finding. The term does not necessarily imply a defined level of certainty regarding the prediction of a particular status or outcome.

When used herein, the term "intact" refers to material that has generally not been substantially disrupted.

When used herein, the term "excised" refers to material that has been removed from its natural location. For example, a breast tissue biopsy specimen is excised to facilitate its examination.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed methods, systems, and examples of which are illustrated in the accompanying Examples and Figures.

Methods

Disclosed herein are methods and systems that make use of light scattering techniques, such as the use of a multiphoton laser-scanning microscope, to quantify the scattering directionality of second harmonic generation (SHG) from biopsy samples of cancer in order to predict efficacy of neoadjuvant chemotherapy. For example, when a patient detects a lump in the breast, or a screening mammogram detects a density, a core needle biopsy is performed and the resultant cylinder of tissue is traditionally sectioned, mounted on a slide, H+E stained, and viewed by a pathologist to determine if a patient has cancer versus something more benign. If cancer is diagnosed, the clinicians must then decide if the breast cancer patient receives neoadjuvant chemotherapy followed by surgery or immediately goes into surgery.

In one example of the methods disclosed herein, the clinician uses the H+E slides already produced in the clinical workflow to assess the SHG directionality, specifically the ratio of forward-to-backwards scattered SHG (F/B) from key areas of the needle biopsy section. In one embodiment, the stroma at the tumor-host interface can be imaged, rather than the bulk of the tumor. Based upon F/B and perhaps some other clinical variables already in use, a score is produced which estimates the likely efficacy of neoadjuvant chemotherapy. This score is then returned to the clinician.

Response to neoadjuvant chemotherapy is rated with an "RCB" score where 0 indicates a pathological complete response, 1 indicates somewhat less than a complete response, while 2 and 3 indicate little or no response, respectively. RCB score is useful as a prognostic predictor of disease-free survival (DFS) and overall survival and is evaluated by the pathologist from examination of the excised tumor bed. Studies of RCB score have shown that reproducibility across pathologist in arriving at this score is very good so evaluating how well SHG F/B correlates with RCB score relies on the high accuracy of RCB score as a early endpoint in the evaluation of neoadjuvant treatment response (Peintinger F, Sinn B, Hatzis C, et al. Reproducibility of residual cancer burden for prognostic assessment of breast cancer after neoadjuvant chemotherapy. Mod Pathol. 2015; 28(7):913-20.) In Example 1, using a completely unoptimized method to quantify F/B from regions in the bulk of tumor tissue as well as at the tumor-host interface in a blinded manner, no correlation between tumor bulk F/B (p=0.95) and an RCB score of 0/1 versus 2/3, but a statistically significant relationship between F/B from the tumor-host interface and an RCB score of 0/1 versus 2/3 (FIG. 4) was found.

Specifically, disclosed herein is a method of treating a subject with cancer, the method comprising: obtaining a sample from cancerous tissue of the subject; preparing the sample for a light scattering test; applying second harmonic generation (SHG) two photon scattering measurements from the sample to determine directionality of scattered photons; obtaining a signature score using selected data from SHG data; determining if the signature score falls above or below a reference level, wherein if the signature score is above the reference level, the subject is treated with neoadjuvant therapy, and if the signature score is below the reference level, the subject is subjected to surgical treatment.

Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma. In one specific example, the cancer can be HER2+, ER+ breast cancer.

In this method, the absolute values of SHG F/B for a specific sample can vary depending upon the optical properties of the system. For example, the value of F and/or B can be affected by: choice of glass slide thickness, choice of forwards detector sensitivity, choice of backwards detector sensitivity, numerical aperture of excitation objective lens, numerical aperture of forward detection lens, etc.). Therefore the absolute value that one will use as a reference level to classify patients into a "treat" or "do not treat" category will vary with the optical system chosen. Someone skilled in the art can adjust reference levels to determine whether a subject is a good candidate for neoadjuvant chemotherapy (likely to benefit from the same) based on the individual setup of the system. For example, each optical detection system can be calibrated using standard reference samples to determine where the cutoff level for the F/B score is, and whether neoadjuvant therapy is indicated for an individual subject. Alternatively, a cohort of patient samples with known outcomes can be used to calibrate an optical system and determine the cutoff level for the F/B score using that system.

For example, in the system used to generate FIG. 4, an F/B ratio under 11 can indicate that the patient would not benefit from neoadjuvant chemotherapy, and other treatment modalities should be sought. In one example, and F/B ratio under 15, 14, 13, 12, 11, 10, 9, or 8 (or any value in between) indicates that neoadjuvant chemotherapy is not a beneficial option. Correspondingly, an F/B ratio above 8, 9, 10, 11, 12, 13, 14, 15, or more, (or any value in between) is indicative that neoadjuvant chemotherapy is useful, and such a treatment should be pursued. The actual cutoff for the SHG F/B ratio for determining neoadjuvant treatment is based on the judgement of the prescribing physician and might vary between patients based on other clinical data independent of SHG F/B scores for that patients and that treatment decision will be informed by larger samples of patients where additional subtype analysis can yield significant results.

ROC curves can also be used to determine neoadjuvant chemotherapy treatment cutoff levels. These can be combined with other predictive measures, as discussed herein.

Optionally, methods of treating a subject based on the results of the assay may further comprise the step of analyzing the test image or test imaging data of the test tissue sample by comparison with one or more reference images or reference imaging data corresponding to a reference tissue sample, such as a sample corresponding to normal (i.e., noncancerous) tissue, for detection and/or characterization. Methods may further comprise the step of generating additional images of the test tissue, including images corresponding to different layers or regions of the test tissue and images generated by different linear and/or nonlinear optical imaging techniques. Optionally, methods of this embodiment include the step of comparing and/or combining different images of the test tissue for the detection and/or characterization of signatures and/or profiles. Reference levels can be determined using samples from previously assayed subjects who have undergone neoadjuvant chemotherapy. Reference levels can also be determined by comparing samples of subjects who were effectively treated with neoadjuvant chemotherapy versus those who were not.

The sample can be provided from a variety of sources known to those of skill in the art. One example is a needle biopsy assay, such as a core needle biopsy. Other examples include, but are not limited to, thin needle biopsy, aspiration biopsy and liquid biopsy. Also disclosed is the use of collagen fragments in an aspiration or liquid biopsy to determine an RCB score, and therefore a reference level.

The subject may have already had a diagnosis of cancer, such as breast cancer, or the subject may be diagnosed with breast cancer using the same biopsy sample used to determine the F/B ratio. For example, a core needle biopsy sample can be obtained from the subject, and used to prognose treatment outcome at the same time that the subject is diagnosed with cancer. Examples of how to obtain a core needle biopsy are known in the art, and can be found in Rocha et al. (Step-by-Step of Ultrasound-Guided Core-Needle Biopsy of the Breast: Review and Technique; Radiol Bras vol. 46 no. 4 São Paulo July/August 2013, herein incorporated by reference in its entirety for its teaching concerning core needle biopsies).

Figure 5:
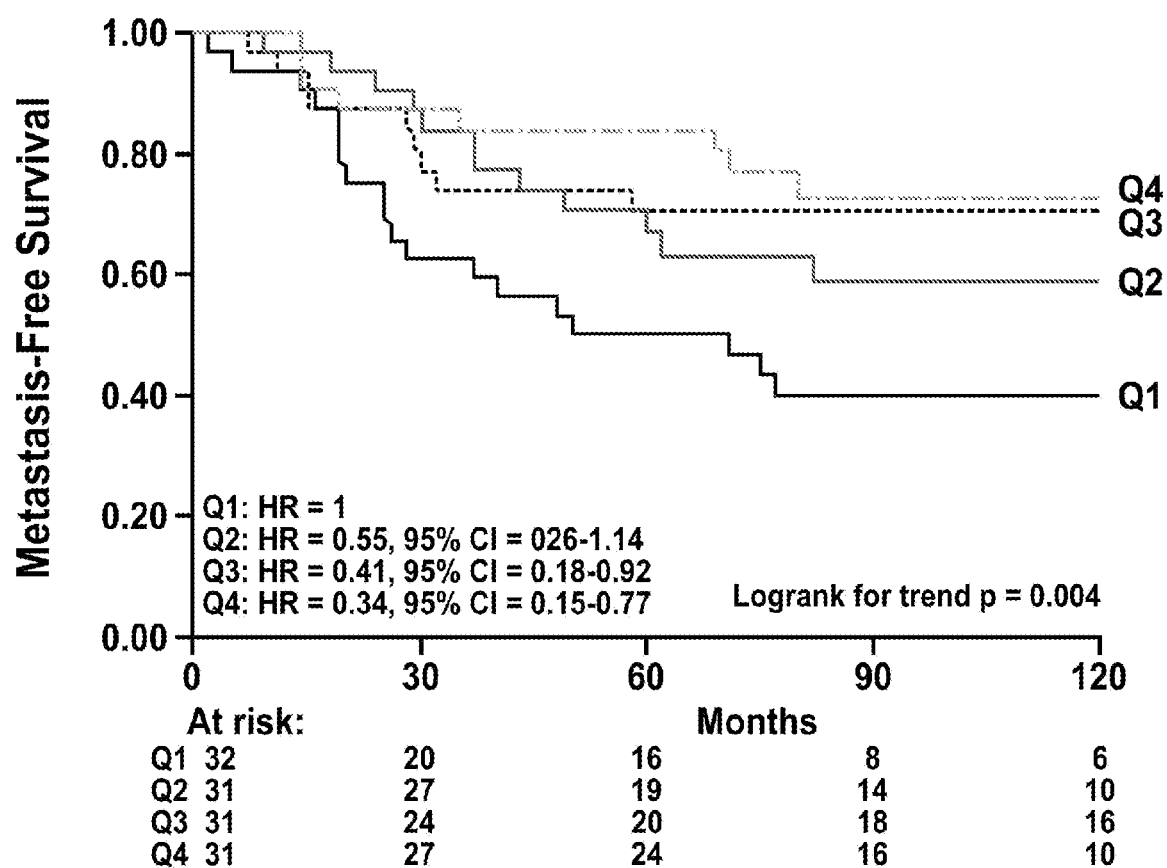
FIG. 5 shows a related method to that disclosed herein, wherein the method uses F/B from primary tumor samples to predict subsequent metastasis, shows F/B as an independent prognostic indicator of 10-year metastasis-free survival in IDC ER+ lymph node negative (NO) patients. Quartile Q1=lowest F/B values and lowest metastasis-free survival. Q4=highest F/B values and the highest number of patients experiencing metastasis-free survival without treatment. Q1 through Q4 in untreated patients stratify risk of recurrence from high to low respectively. It should be noted that Q4 with the highest values of F/B measured and the least likelihood to recur without treatment in these ER+NO breast cancer patients also appear to correspond to the patients most likely to experience pCR when treated with neoadjuvant chemotherapy for both HER2+ and luminal A patient groups based on having the values for F/B. This result was unexpected as it is not obvious that patients selected as high risk for metastatic recurrence and therefore offered neoadjuvant chemotherapy before surgery would be most likely to respond to treatment if they are also at lower risk for metastatic recurrence as determined by F/B quartile.

After the sample is collected, it can be imaged using SHG. SHG is an intrinsic optical signal in which two incoming photons scatter off of material, producing one emission photon of half the incoming wavelength (FIG. 1). In tumors, SHG is generated by fibrillar collagen and is sensitive to the microscopic structure of the scattering material. Hence SHG emission directionality is sensitive to the diameter of the fibrils that are bundled into collagen fibers, as well as their spacing within the fiber, and the disorder in their packing (Han X. Burke R M, Zettel M L, Tang P. Brown E B: Second harmonic properties of tumor collagen: determining the structural relationship between reactive stroma and healthy stroma. Optics express 2008, 16(3):1846-1859. Lacomb R, Nadiarnykh O, Townsend S, Campagnola P J: Phase Matching considerations in Second Harmonic Generation from tissues: Effects on emission directionality, conversion efficiency and observed morphology. Optics communications 2008, 281(7):1823-1832. Williams R M, Zipfel W R, Webb W W: Interpreting second-harmonic generation images of collagen I fibrils. Biophysical journal 2005, 88(2):1377-1386). The ratio of the forward-emitted to backward-emitted SHG (where "forward" is the direction of the incident excitation laser) is known as the F/B ratio and is sensitive to these structural properties of collagen fibers (FIG. 5).

It has previously been shown that the average F/B of patient biopsy samples can differentiate healthy and breast tumor tissue, and changes with tumor grade and stage (Burke K, Tang P, Brown E. (2013) SHG Reveals Matrix Alterations During Breast Tumor Progression. J Biomed Optics. 18(3) 031106); US20170020462A1, all incorporated herein by reference in their entirety for their teaching concerning SHG imaging of cancer tissue). Since SHG is an intrinsic optical signature, measurements of F/B can be performed on typical pathology slides without additional contrast reagents. Furthermore, determination of the average F/B in a sample involves only a straightforward, automated application of pixel intensity analysis that does not require a trained observer.

Methods of generating an F/B ratio from a sample using SHG are known in the art. For example, U.S. Pat. No. 8,812,085 (Brown et al.), and U.S. Patent Application No. US20170020462A1 (Brown et al.), herein incorporated by reference in their entirety, teaches systems and methods for determining F/B ratio from a sample. The method used to generate the data in FIG. 4 is as follows. A conventional multiphoton laser-scanning microscope illuminated a region of interest in a sample with 810 nm pulsed excitation light (100 fs pulses, 80 MHz repetition rate). SHG light was collected in the backwards-propagating direction by the excitation objective lens, while forward-propagating SHG light was collected by a second objective lens placed upon the opposite side of the sample from the excitation objective lens and aligned colinearly with it. Collected light was directed by each objective lens through an appropriate color filter (to reject laser light and pass SHG) and then to a corresponding detector (in the case of FIG. 4 these detectors were photomultiplier tubes but any other light sensor is appropriate, e.g avalanche photodiode, etc.), and a forwards-SHG and backwards-SHG image generated and saved. Next, background was subtracted from each image, and an intensity-based threshold was determined by a blinded user which rejected dim (i.e. background) pixels from each image. Remaining pixels were ratioed to generate an F/B value for each pixel, and the average F/B value of all remaining pixels was calculated.

Solid tumors have a distinct structure that mimics that of normal tissues and comprises two distinct but interdependent compartments: the parenchyma (neoplastic cells), ("tumor bulk" in FIG. 4) and the stroma that the neoplastic cells induce and in which they are dispersed, are referred to as the "tumor-host interface" in FIG. 4. SHG F/B can be carried out at the interface between the tumor cell parenchyma and the tumor stroma next to tumor bulk containing more cancer cells than stroma. For example, the tissue sample can comprise 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96 97, 98, 99, or 100% cancer cells. In one example, the tumor tissue sample can be excised and examined so that both tumor parenchyma and surrounding tumor stoma are included. The interface between the two can then be imaged, and the SHG F/B ratio at or near the intersection can be calculated.

The method of preparing the tissue sample for testing can be carried out in a variety of ways known to those of skill in the art. For example, the sample can be obtained from a subject via core needle biopsy. The sample can then be sectioned, mounted on a slide, and stained, such as with hematoxylin and eosin (H+E). The SHG methods disclosed herein can then be used to determine the F/B scattering ratio.

If the subject receives a score that shows that neoadjuvant therapy is the recommended course of action, the subject can be treated accordingly. Examples of neoadjuvant therapy include chemotherapy, radiation therapy, and hormone therapy. Neoadjuvant chemotherapy, as used herein, refers to an anticancer drug treatment performed on a patient suffering from cancer for the purpose of reducing the size of tumor tissues and the like prior to a surgery. One of skill in the art can ascertain and treat a subject with neoadjuvant chemotherapy based on the specific type of cancer and specific needs of the subject. Therefore, the agent used for neoadjuvant chemotherapy is not limited, and a skilled physician can readily assess when, how, and what type of neoadjuvant chemotherapy to administer.

Types of neoadjuvant chemotherapy include, but are not limited to, anthracycline- and taxane-based therapies. For breast cancer, neoadjuvant therapy can include a combination of the targeted therapy drugs trastuzumab and pertuzumab, or one or the other. Other types of neoadjuvant chemotherapy includes paclitaxel, docetaxel, epirubicin, cyclophosphamide, 5-fluorouracil, adriamycin, ixabepilone, anthracycline and the like. In neoadjuvant chemotherapy, one or a combination of two or more of these agents can be administered to a subject according to a prescribed schedule.

A subject who undergoes neoadjuvant chemotherapy can also undergo other treatments, either before, after, or during neoadjuvant chemotherapy. For example, the subject can receive neoadjuvant radiation therapy, and/or hormone therapy. The subject can undergo surgery after neoadjuvant therapy, and can also undergo adjuvant chemotherapy and/or radiation therapy. One of skill in the art can recommend a treatment pathway for an individual based on the results of the assay described herein.

In vivo application of neoadjuvant chemotherapy can be accomplished by any suitable method and technique presently or prospectively known to those skilled in the art. For example, compounds or compositions for neoadjuvant chemotherapy can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the compounds or compositions can be a single administration, or at continuous or distinct intervals as can be readily determined by a person skilled in the art.

The compounds or compositions for neoadjuvant chemotherapy can also be administered utilizing liposome technology, slow release capsules, implantable pumps, and biodegradable containers. These delivery methods can, advantageously, provide a uniform dosage over an extended period of time.

The compounds or compositions for neoadjuvant chemotherapy can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds or compositions for neoadjuvant chemotherapy can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions for neoadjuvant chemotherapy disclosed herein can include other agents conventional in the art having regard to the type of formulation in question.

For the treatment of oncological disorders, the compounds or compositions for neoadjuvant chemotherapy can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, a composition for neoadjuvant chemotherapy can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies can also be used.

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent.

Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

For the treatment of oncological disorders, neoadjuvant chemotherapeutic agents, such as those disclosed herein, can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.)

The assessment of treatment for a subject can also be based on other risk factors. In other words, the signature score for a subject can also calculated based on factors other than the SHG F/B ratio. For example, both genetic factors and non-genetic factors can be used to make this determination. The score can also be based on Magee score or derivatives that predict Oncotype DX 21 gene assay recurrence score.

Genetic factors, as used herein, refer to factors that are measured by genotyping and may include an individual's genotype profile, particularly polymorphic profile. Polymorphism refers to the co-existence of multiple forms of a genetic sequence in a population. The most common polymorphism is Single Nucleotide Polymorphism ("SNP"), a small genetic variation within a person's DNA sequence. SNPs occur frequently throughout the human genome. They are often associated with, or located near a gene found to be associated with, a certain disease. Thus, SNPs are genetic markers indicative of genetic disease risk factors as they mark the existence and locations of genes that render an individual susceptible to a disease. Since SNPs tend to be genetically stable, they are excellent genetic markers of diseases. For examples of known methods of assessing disease risks based on genetic markers see U.S. Pat. No. 6,162,604 to Jacob; U.S. Pat. No. 4,801,531 to Frossard; and U.S. Pat. No. 5,912,127 to Narod and Phelan, all of which are incorporated herein for their teaching concerning assessing risk based on genetic markers.

Non-genetic factors refer to factors that are not measured by genotyping, such as age, sex, race, family history, previous cancer history, height and weight, as well as environmental factors and lifestyle, such as smoking habit and living conditions.

Tumor-specific measures such as tumor size, ER, PR, HER2 status, heterogeneity as measured by differenced detected for different parts of a tumor and migration of cells with a particular expression profile, calcium apatite, nuclear grade, and multiple other pathological staging criteria known to those of skill in the art can also be used in treatment decisions in an attempt to determine the best treatment outcome in the subject.

Systems

Disclosed herein is a system for evaluating a sample of tissue from a subject with cancer to determine treatment outcome using neoadjuvant chemotherapy, comprising: an SHG optical imaging device for generating correlated test image pairs in the forward and backward direction or test imaging data from the sample where each pixel represents the ratio of the forward to backward two photon light scatter intensities or photon counts from SHG; and a processor for analyzing said test image pairs or test imaging directional data from a point by point measurement of the sample, said processor using a quantitative algorithm for analyzing said test image or test imaging directional data for detection of a signature distribution of values from a region of interest (ROI) related to treatment outcome using neoadjuvant chemotherapy, wherein said signature distribution of values is used to generate a signature score, wherein said calculation from image data is used to generate a signature score.

In embodiments of the present invention, analysis may be carried out by a doctor, other healthcare professional, researcher, a computer or computer processor, or any combination of these. For example, the tissue sample can be collected by an attending physician, then sent to a laboratory for diagnosis/prognosis results where, at this time, the SHG F/B ratio can be obtained for the sample.

In one embodiment providing a partially or fully automated method, identification of the signature score is carried out via a computer-based technique employing pattern recognition analysis of one or more images of the test tissue to identify the tumor host interface where the SHG F/B ratio should be calculated, as described herein. A computer can be used to accomplish all the steps of the present methods with final clinical staff oversight, or a computer may be used to perform only a certain step or selected series of steps in the present methods. The present invention includes partial and fully automated methods for diagnosing cancer in tissues.

Pattern recognition using machine learning can also include "deep learning," where no preselection of thresholds or other direction is given to bias the outcome. Machine learning algorithms can then be applied to the image pairs (F and B images) with known outcomes (RCB scores) to determine the optimal method for distilling each image pair into a predictive score based on SHG F/B from the pixels identified as containing the predictive signal. This is referred to herein as a "machine learning algorithm" to recognize features based on the whole dataset, where the known outcome of treatment is used to develop a classifier for those who respond.

The processor can be trained based on a reference set of image data from those effectively treated and those who failed treatment and using directed or undirected machine learning to obtain a classifier which identifies in new unknown samples those who will effectively be treated in the future.

The control value can be a numerical threshold for predicting outcomes. In some embodiments, a test value or combined score is predictive, for example, of a subject who can benefit from neoadjuvant chemotherapy, whereas a different combined score is predictive, for example, of a subject who would not benefit from neoadjuvant chemotherapy. This is discussed in greater detail in the "methods" section, above.

Subjects may be classified on the basis of threshold values (signature scores) or based upon Mean and/or Median expression levels in high risk patients versus low-risk patients. Various classification schemes are known for classifying samples between two or more classes or groups, and these include, without limitation: Principal Components Analysis, Naive Bayes, Support Vector Machines, Nearest Neighbors, Decision Trees, Logistic, Artificial Neural Networks, Penalized Logistic Regression, and Rule-based schemes. In addition, the predictions from multiple models can be combined to generate an overall prediction. For example, a "majority rules" prediction may be generated from the outputs of a Naive Bayes model, a Support Vector Machine model, and a Nearest Neighbor model.

Thus, a classification algorithm or "class predictor" may be constructed to classify samples. The process for preparing a suitable class predictor is reviewed in R. Simon, Diagnostic and prognostic prediction using gene expression profiles in high-dimensional microarray data, British Journal of Cancer (2003) 89, 1599-1604, which review is hereby incorporated by reference in its entirety.

In a further aspect, the application provides computer programs and computer implemented products for carrying out the methods described herein. Accordingly, in one embodiment, the application provides a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the methods described herein.

EXAMPLES

Example 1: Using Multiphoton Laser Scanning Microscopy to Assess Neoadjuvant Therapy Outcomes in Core Needle Biopsies Over-expression of Human Epidermal Growth Factor receptor-2 (HER2) in breast cancer is associated with an aggressive clinical course and poor prognosis. Certain subsets of HER2+ patients may receive trastuzumab—based neoadjuvant chemotherapy; however, a number of these patients do not respond well to this treatment and would instead benefit from immediate surgical resection of the tumor. Thus, there is a need to predict which individuals are likely to respond well to trastuzumab—based neoadjuvant chemotherapy. One candidate for a predictor of patient response is the quantification of collagen microstructure by a light scattering phenomenon known as second-harmonic generation (SHG). (Burke et al. BMC Cancer 15 (2015): 929). Disclosed herein is the evaluation of the ability of this quantitative methodology to predict pathological response after neoadjuvant HER2-targeted treatment as assessed by the Residual Cancer Burden (RCB) score/class. This quantitative evaluation in pre-treatment biopsies, is then correlated with the pathologic response to treatment in the post-therapy resection.

Second-harmonic generation (SHG) is a nonlinear optical process that occurs when two photons of the same frequency interact with certain materials. In solid tumors, the only significant source of SHG is fibrillar collagen. SHG imaging is: rapid (<10 s per scan), non-destructive, and can be performed on fixed or fresh tissue.

SHG F/B has been shown to stratify IDC ER+N0 tumors based on their potential to metastasize and tumor aggressiveness (Burke et al.) Therefore, this quantitative technique was applied to pre-neoadjuvant HER2+ core needle biopsies taken prior to trastuzumab-based neoadjuvant chemotherapy to see how F/B correlates with a patient's post-neoadjuvant response, as scored using the Residual Cancer Burden (RCB) class.

Clinical pathologic variables for 29 cases of HER2-positive breast cancer that had undergone neoadjuvant chemotherapy plus HER2-positive therapy were retrieved, including the post-treatment RCB score and ER/PR/HER2 status. Second hamonic generation (SHG) is an intrinsic optical signal produced by fibrillar collagen. To quantify collagen microstructure in the pre-treatment core biopsy, SHG imaging was used to determine the average forward-to-backward light-scattering ratio (F/B). The F/B ratio is sensitive to structural properties of collagen fibers (FIGS. 1 and 5).

Figure 2:
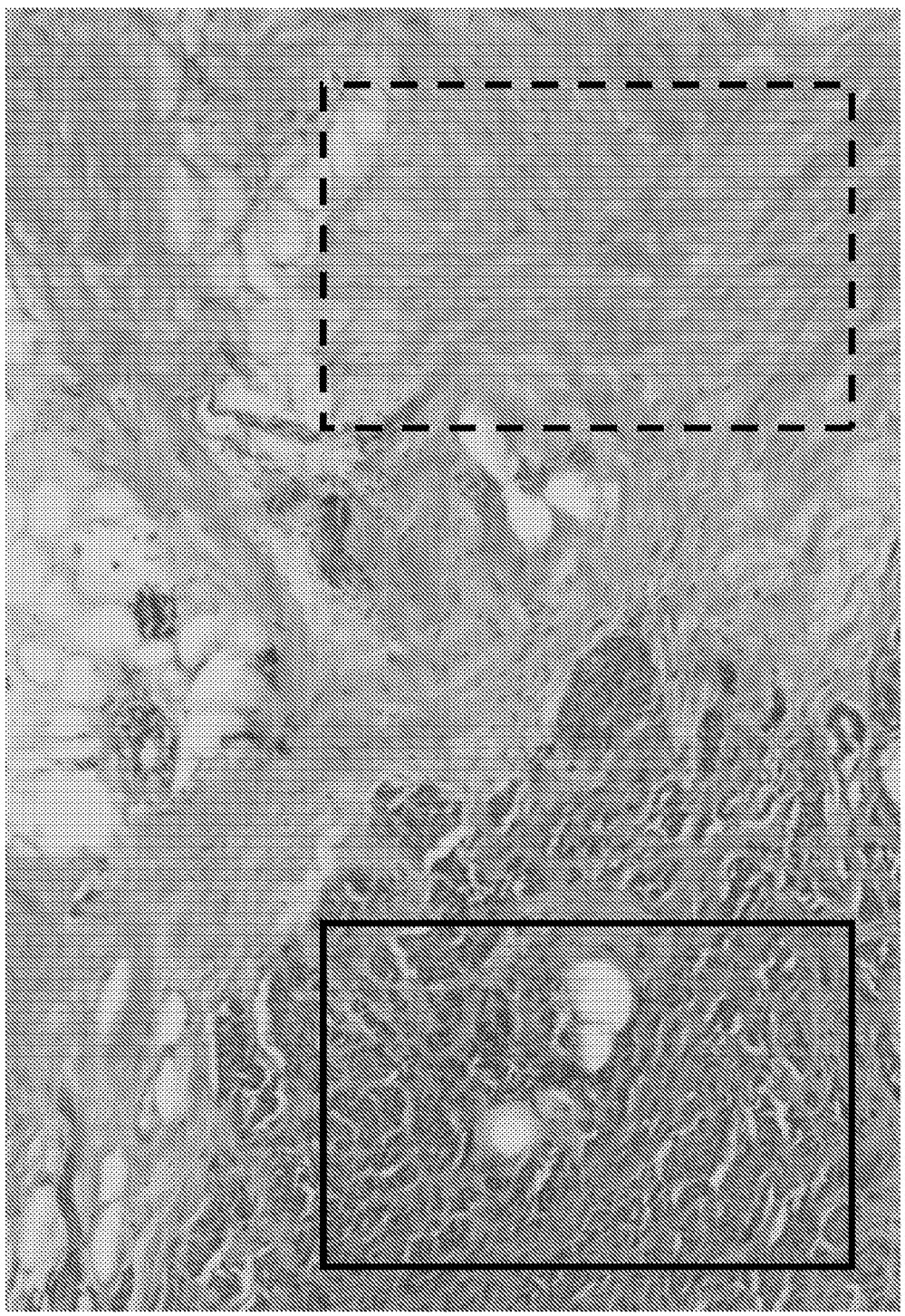
FIG. 2 shows core needle biopsies of tumor tissue showing an area containing mostly cancer cells referred herein as the tumor bulk and surrounding tumor stroma with tumor associated fibroblasts and collagen at the tumor-host interface. Pretreatment core needle biopsies were taken from 29 HER2+ patients. These contain both the bulk of the patient's tumor and regions of the tumor-host interface, consisting mainly of fibrillar collagen. Three images were taken in both the tumor bulk (solid box) and tumor-host interface (dashed box) for each biopsy (6 images per patient).
Figure 4A:
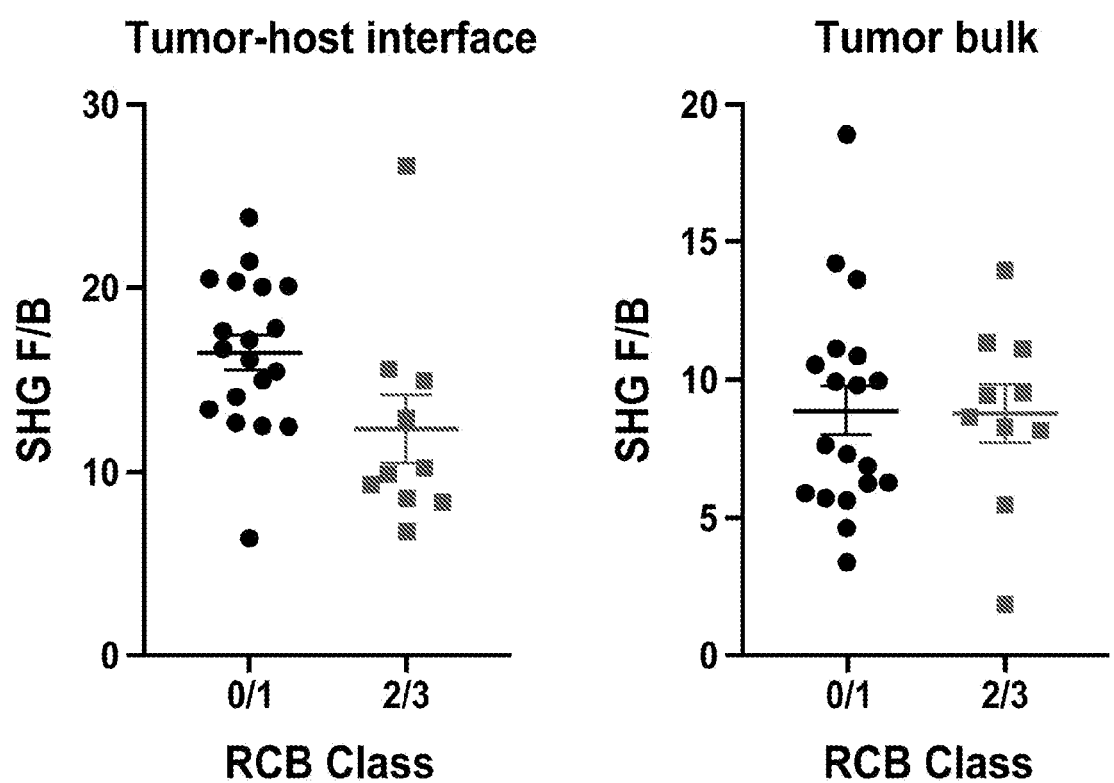

Logistic regression was used to assess the association between F/B and the binary response variable RCB class (0/1 or 2/3) (FIG. 4A). A likelihood ratio test was used to calculate the p-value (p=0.035) for the test of whether the regression coefficient for F/B was zero (i.e., no effect) in the tumor-stroma interface. The average F/B ratio at the leading edge of the tumor stromal interface stratified by RCB class is shown in Table 1. When evaluated in the bulk of the tumor tissue, F/B was not correlated with RCB status; however, when evaluated at the leading edge of the tumor stromal interface, F/B was correlated with RCB status (FIGS. 2 and 3).

TABLE 1

Average F/B Ratio in HER2+ breast cancer by RCB Class

| RCB Class (n) | Average F/B ± SEM |
| --- | --- |
| 0/1 (19) | 16.95 ± 1.06 |
| 2/3 (10) | 12.32 ± 1.84 |

A second population of 35 luminal A breast cancer patients (ER+, HER2−) was similarly studied using logistic regression to assess the association between F/B and the binary response variable RCB class (0/1 or 2/3) (FIG. 4C). This population had many fewer patients with a RCB Class score of 0/1 with 7 out of 35 (Table 2) compared to 19 out of 29 for the HER2+ patient group (Table 1). A likelihood ratio test was used to calculate the p-value (p=0.0404) for the test of whether the regression coefficient for F/B was zero (i.e., no effect) in the tumor-stroma interface. The average F/B ratio at the leading edge of the tumor stromal interface stratified by RCB class is shown in Table 2. When evaluated in the bulk of the tumor tissue, F/B was not correlated with RCB status; however, when evaluated at the leading edge of the tumor stromal interface, F/B was correlated with RCB status.

TABLE 2

Average F/B Ratio in luminal A breast cancer by RCB Class

| RCB Class (n) | Average F/B ± SEM |
|---|---|
| 0/1 (7) | 13.77 ± 0.96 |
| 2/3 (28) | 10.07 ± 0.74 |

It has previously been shown that the measurement of F/B in the primary tumor after resection is an independent prognostic indicator of metastasis-free survival in breast cancer. The results disclosed herein further shows that the evaluation of microstructure of collagen fibers, specifically at the tumor/stroma interface by F/B measurement from the pre-treatment biopsy, can be useful for predicting pathologic response to trastuzumab-based neoadjuvant therapy, as well as other types of neoadjuvant therapy.

database. These patients' rMBC outcomes using logistic regression and Kaplan-Meier (KM) analysis.

Recent reporting of the 9 year follow-up for the TAILORx trial suggested that there may be no benefit with adjuvant chemotherapy for ER+, HER2−, N(0) invasive ductal carcinoma (IDC) breast cancer patients with a Oncotype DX* (ODX) recurrence score (RS)<26 (except for a few women under 50 years old). Since endocrine therapy for this group of patients who comply with treatment still results in distance recurrence (rMBC) in 3% and 5% of the ODX low and ODX intermediate risk groups at 9 years, respectively, it is desired that early treatments be given for these patients by identifying their recurrence risk at diagnosis with improved risk stratification.

OPTIM alone stratified at 2.5× relative risk (RR) between quartiles Q1 and Q4 in Table 3, similar to S-ODX low vs. high recurrence score (RS) groups (from TAILORx Trial) with 2.8×RR. Using quartiles of OPTIM vs. 5-ODX together, patients were stratified to recurrence risk (rMBC at Risk1) with an improved risk stratification of 5×RR in the RS<26 lower risk groups.

TABLE 3

OPTIM (Quartiles) Stratify S-ODX Low Risk Groups Defined in TAILORx Trial
OPTIM (Quartiles) Stratify S-ODX Low Risk Groups Defined in TAILORx Trial

| S-ODX → | High (RS > 25) | Intermediate (RS 11-25) | Low (RS < 11) | All |
|---|---|---|---|---|
| OPTIM | ↓ | ↓ | ↓ | ↓ |
| Q1 | 7/9 = 78% | 7/12 = 58%* | 5/10 = 50% | 19/31 = 61%* |
| Q2 | 5/9 = 56% | 5/14 = 36% | 2/8 = 25% | 12/31 = 39% |
| Q3 | 8/12 = 67%*** | 1/8 = 13% | 1/11 = 9%*** | 10/31 = 32% |
| Q4 | 6/10 = 60%** | 2/17 = 12%* | 0/5 = 0%** | 8/32 = 25%* |
| All | 26/40 = 65%* | 15/51 = 29% | 8/34 = 24%* | 49/125 = 39% | rMBC/(at risk) at 10 years by KM analysis
*$p < 0.05$,
**$p < 0.005$,
***$p < .0005$

Example 2: Optical Prediction of Time Interval to Metastasis (OPTIM): A Rapid Nondestructive Optical Assay Applied to Tissue Microarray Samples Identifying High Risk of Distant Recurrence in the Lowest Risk Groups Defined by the TAILORx Trial Also disclosed herein is a optical prediction method that improves the prediction of recurrence for distant metastatic recurrence (rMBC) when using a commercially available gene expression assay, Oncotype Dx in a subject who has not received any treatment except surgical resection. This shows that SHG F/B ratios can be generated and used in a manner that allows for prediction of various diagnostic features related to cancer prognosis. For this example with breast cancer the data supports that OPTIM is independent or adds additional information and value to available methods.

Optical Prediction of Time Interval to Metastasis (OPTIM), a novel assay, prognostic for rMBC, is based on an intrinsic optical signature from collagen, derived from the average of point by point ratios of forward to backward (F/B) second harmonic generation (SHG) light scatter that is sensitive to form and structure of fibrillar collagen in the extracellular matrix of archival tissue microarray samples 1. OPTIM currently is based on only the log natural (ln) of F/B and is a normally distributed parameter. The 125 patients in this cohort were part of a clinical study, looking for genomic predictors of rMBC in untreated patients, so a surrogate 21-gene RT-PCR assay (S-ODX) value was calculated based on gene expression data available through NCBI GEO Combining S-ODX with OPTIM, low (L) or high (H) risk by assay in Table 4, shows that they are independent and complementary. Notably 68%=85/125 adults are classified L by S-ODX (RS<26) and OPTIM effectively reclassifies H and L, and when combined with S-ODX, H identifies 92%=45/49 of all rMBC at 10 years without treatment. Risk stratification improves to 6.8×RR comparing highest risk HH 66.7%=12/18 to lowest risk LL 9.8%=4/41.

By combining S-ODX with OPTIM to stratify risk of metastatic recurrence in untreated patients we identify those patients who are most likely to benefit from further treatment. ODX is on the market and is successfully used in treatment decisions to select those patients who have a measurable response to adjuvant chemotherapy in about one third of all patients diagnosed with ER+ HER2− IDC breast cancer. OPTIM based on F/B divides this treatment group in half with either HH or HL as shown in Table 4. Based on the fact that those who respond with pCR in the neoadjuvant treatment setting (as shown in Example 1) have high values of F/B in Q4 of the distribution of F/B based signature scores it is likely that F/B can be used to predict response to chemotherapy in the those assigned to adjuvant chemotherapy based on ODX. This possibility can be readily confirmed by obtaining archived tissue from the TAILORx trial (or other trials where there is randomization of adjuvant chemotherapy and a measured ODX recurrence score) and (blind to outcome) measure OPTIM (F/B based signature score) and quantify (when unblinded to outcome after making the measurements) the benefit of using OPTIM to further predict response to treatment with adjuvant chemotherapy.

Furthermore, in the two thirds of patients who were shown not to benefit from adjuvant chemotherapy in the TALORx trial, OPTIM is able to identify in half of those patients the people at highest risk for recurrence without further treatment in addition to the third who are LL in table 3 and are at low enough risk of recurrence that treatment benefit is unlikely to be measurable.

In these two examples we have described how a signature score based on F/B and combined with other independent predictors could be combined into the best predictor of treatment response which we call OPTIM. There are many treatments offered to patients and many ongoing clinical trials to obtain the evidence for improved treatment decisions for the individual patient. In the manner described herein we describe a new way to improve treatment decisions by using a signature score based on F/B on initial biopsy tissue from each patient to increase the likelihood of the desired treatment outcome which is response to treatment.

TABLE 4

Distant Recurrence Identified by High Risk Group of Each Assay
Distant Recurrence Identified by High Risk Group of Each Assay

| S-ODX Assay | H | H | L | L |
|---|---|---|---|---|
| OPTIM Assay | H | L | H | L |
| rMBC (total = 49 = 100%) | 12 = 24% | 14 = 29% | 19 = 39% | 4 = 8% |
| At Risk (total n = 125 = 100%) | 18 = 14% | 22 = 18% | 44 = 35% | 41 = 33% | rMBC at 10 yrs.
S-ODX RS > 25 = H,
RS < 26 = L;
OPTIM Q1&Q2 = H,
Q3&Q4 = L

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

REFERENCES

[1] Pantazis P, Maloney J, Wu D, Fraser S E. Second harmonic generating (SHG) nanoprobes for in vivo imaging. *Proceedings of the National Academy of Sciences of the United States of America.* 2010; 107(33):14535-14540. doi:10.1073/pnas.1004748107.
[2] Han X, Burke R M, Zettel M L, Tang P, Brown E B. Second harmonic properties of tumor collagen: determining the structural relationship between reactive stroma and healthy stroma. Opt Express. 2008; 16(3):1846-59. PubMed PMID: 18542263.
[3] Williams R M, Zipfel W R, Webb W W. Interpreting second-harmonic generation images of collagen I fibrils. Biophys J. 2005; 88(2):1377-86. doi: 10.1529/biophysj.104.047308. PubMed PMID: 15533922; PMCID: PMC1305140.
[4] Burke K, Smid M, Dawes R P, et al. Using second harmonic generation to predict patient outcome in solid tumors. *BMC Cancer.* 2015; 15:929. doi:10.1186/s12885-015-1911-8.
[5] Sage, D. OrientationJ: A series of ImageJ plugins for directional image analysis. Biomedical Image Group at EPFL, Switzerland.

What is claimed is:
1. A method of treating a subject with cancer, the method comprising:
   a. obtaining a sample from cancerous tissue of the subject;
   b. preparing the sample for a light scattering test;
   c. applying second harmonic generation (SHG) two photon scattering measurements from the sample to determine directionality of scattered photons;
   d. obtaining a signature score using selected data from SHG data;
   e. determining if the signature score falls above or below a reference level, wherein if the signature score is above the reference level, the subject is treated with neoadjuvant therapy, and if the signature score is below the reference level, the subject is subjected to surgical treatment.
2. The method of claim 1, wherein the sample is a needle biopsy sample.
3. The method of claim 2, wherein the needle biopsy sample is a core needle biopsy sample.
4. The method of claim 1, wherein the cancer is breast cancer, prostate cancer, or thyroid cancer.
5. The method of claim 4, wherein the breast cancer is HER2+ and ER+ breast cancer.
6. The method of claim 1, wherein the subject was diagnosed with cancer before the method of claim 1 is carried out.
7. The method of claim 1, wherein the subject is diagnosed with cancer after the sample is obtained and prepared.
8. The method of claim 1, wherein SHG is carried out at the tumor-host interface in collagen rich tumor stroma next to tumor bulk containing more cancer cells than stroma.
9. The method of claim 1, wherein the sample of step b) is prepared by:
   i. sectioning the sample;
   ii. mounting the sample on a slide; and
   iii. staining the slide with hematoxylin and eosin (H+E).
10. The method of claim 1, wherein SHG is used to determine forwards-to-backwards (F/B) scattering ratio.
11. The method of claim 1, wherein SHG is carried out using a multiphoton laser-scanning microscope.
12. The method of claim 1, wherein the subject who undergoes neoadjuvant chemotherapy later undergoes surgery as well.
13. The method of claim 1, wherein the signature score is also calculated based on the age, sex, race, family history, and/or lifestyle of the subject.
14. The method of claim 1, wherein the signature score is also calculated based on genetic markers of the subject.
15. The method of claim 1, wherein said reference levels are determined using samples from previously assayed subjects who have undergone neoadjuvant chemotherapy.

16. The method of claim 1, wherein the reference levels are determined by comparing samples of subjects who were effectively treated with neoadjuvant chemotherapy versus those who were not.

* * * * *